(12) United States Patent
Kawamura et al.

(10) Patent No.: US 8,039,090 B2
(45) Date of Patent: Oct. 18, 2011

(54) POROUS COMPOSITE CONTAINING CALCIUM PHOSPHATE AND PROCESS FOR PRODUCING THE SAME

(75) Inventors: Katsumi Kawamura, Tokyo (JP); Takehiko Nakajima, Tokyo (JP); Daisuke Shoji, Tokyo (JP); Junzo Tanaka, Tsukuba (JP); Masanori Kikuchi, Tsukuba (JP); Toshiyuki Ikoma, Tsukuba (JP)

(73) Assignees: Hoya Corporation, Tokyo (JP); National Institute for Materials Science, Ibaraki (JP)

( * ) Notice: Subject to any disclaimer, the term of this patent is extended or adjusted under 35 U.S.C. 154(b) by 1010 days.

(21) Appl. No.: 10/558,245

(22) PCT Filed: May 26, 2004

(86) PCT No.: PCT/JP2004/007169
§ 371 (c)(1),
(2), (4) Date: Apr. 25, 2006

(87) PCT Pub. No.: WO2004/103422
PCT Pub. Date: Feb. 12, 2004

(65) Prior Publication Data
US 2006/0292350 A1 Dec. 28, 2006

(30) Foreign Application Priority Data
May 26, 2003 (JP) .................. 2003-147770

(51) Int. Cl.
*B32B 3/00* (2006.01)
(52) U.S. Cl. ........................ 428/189; 428/220
(58) Field of Classification Search .................. 427/2.27; 428/189, 220
See application file for complete search history.

(56) References Cited

U.S. PATENT DOCUMENTS 4,629,464 A    12/1986 Takata et al.
(Continued)

FOREIGN PATENT DOCUMENTS

EP    1155705    11/2001
(Continued)

OTHER PUBLICATIONS

Oxford English Dictionary, "flange, n.", Oxford University Press, 2010, accessed on Jan. 4, 2010 from dictionary.oed.com/cgi/entry/50085702?query_type=word&queryword=flange&first=1&max_to_show=10&sort_type=alpha&search_id=Lchg-sdeC6p-4139&result_place=1&case_id=Lchg-kH7arN-4140&p=1&d=1&sp=1&qt=1&ct=0&ad=1&print=1.*

(Continued)

*Primary Examiner* — David Sample
*Assistant Examiner* — Tahseen N Khan
(74) *Attorney, Agent, or Firm* — Greenblum & Bernstein, P.L.C.

(57) ABSTRACT

A porous composite comprising a porous layer containing a calcium phosphate ceramic, and a dense layer formed on part of the porous layer and having a smaller average pore size than that of the porous layer. The porous composite can be produced by (1) introducing a slurry containing a calcium phosphate ceramic/collagen composite and collagen into a molding die having a high thermal conductivity, (2) rapidly freezing and drying the slurry in the molding die, to form a porous body comprising a porous layer and a dense layer formed on the porous layer, (3) cross-linking collagen in the porous body, and (4) removing the dense layer except for a portion thereof on a surface coming into contact with a soft tissue when implanted in a human body, so that the porous layer is exposed.

11 Claims, 2 Drawing Sheets

U.S. PATENT DOCUMENTS

| | | | |
|---|---|---|---|
| 4,969,913 A | | 11/1990 | Ojima |
| 5,017,518 A | | 5/1991 | Hirayama et al. |
| 5,064,436 A | | 11/1991 | Ogiso et al. |
| 5,082,803 A | | 1/1992 | Sumita |
| 5,089,195 A | | 2/1992 | Ichitsuka et al. |
| 5,171,720 A | | 12/1992 | Kawakami |
| 5,665,295 A | * | 9/1997 | Takamoto et al. ....... 264/172.19 |
| 5,776,193 A | | 7/1998 | Kwan et al. |
| 6,019,764 A | * | 2/2000 | Bartee ......................... 606/86 R |
| 6,187,046 B1 | | 2/2001 | Yamamoto et al. |
| 6,187,047 B1 | | 2/2001 | Kwan et al. |
| 6,203,574 B1 | | 3/2001 | Kawamura |
| 6,355,699 B1 | | 3/2002 | Vyakarnam et al. |
| 6,613,091 B1 | * | 9/2003 | Zdeblick et al. ............ 623/17.16 |
| 6,733,528 B2 | | 5/2004 | Abe et al. |
| 6,764,517 B2 | | 7/2004 | Yamamoto et al. |
| 6,887,272 B2 | * | 5/2005 | Shinomiya et al. ........ 623/17.11 |
| 6,902,584 B2 | | 6/2005 | Kwan et al. |
| 2002/0022885 A1 | | 2/2002 | Ochi |
| 2002/0120348 A1 | | 8/2002 | Melican et al. |
| 2003/0077311 A1 | | 4/2003 | Vyakarnam et al. |
| 2003/0193104 A1 | | 10/2003 | Melican et al. |
| 2004/0096475 A1 | | 5/2004 | Hiraide et al. |
| 2004/0220680 A1 | | 11/2004 | Yamamoto et al. |
| 2005/0246032 A1 | | 11/2005 | Bokros et al. |
| 2005/0271695 A1 | | 12/2005 | Kikuchi et al. |
| 2006/0013894 A1 | | 1/2006 | Yamamoto et al. |

FOREIGN PATENT DOCUMENTS

| | | | |
|---|---|---|---|
| EP | 1 216 717 | | 6/2002 |
| JP | 61-079463 | | 4/1986 |
| JP | 2-167868 | | 6/1990 |
| JP | 8-048583 | | 2/1996 |
| JP | 3048289 | | 3/2000 |
| JP | 2002-102328 | | 4/2002 |
| JP | 2002 102328 | | 4/2002 |
| JP | 2002-200085 | | 7/2002 |
| JP | 2004-205961 | | 7/2004 |
| WO | 97/14376 | | 4/1997 |
| WO | 98/22154 | | 5/1998 |
| WO | 00/21470 | | 4/2000 |
| WO | 01/02033 | | 1/2001 |
| WO | WO 02065955 A1 | * | 8/2002 |
| WO | WO 2004000174 A1 | * | 12/2003 |
| WO | 2004/041320 | | 5/2004 |

OTHER PUBLICATIONS

English Language Abstract of JP 2002 102328, (Apr. 2000).

English Language Abstract of JP 8-048583.

Ryuji Kato et al., "Preparation of Hydroxyapatite Ceramics with One-Dimensional Pores Using Freeze-dry Process," Dai 6 Kai Seitai Kanren Ceramics Toronkai Koen Yokosyu, 2002 Nen, p. 22 (with English abstract).

Chang et al., "Preparation of a porous hydroxyapatite/Collagen Nanocomposite using glutaraldehyde as a crosslinking agent," J. Mat. Sci. Let., 2001, vol. 20, No. 13, pp. 1199-1201.

International Preliminary Search Report and Written Opinion of the International Searching Authority for International Application No. Application No. PCT/JP2004/007169.

Japanese Office Action (Notice of Reason for Refusal) dated Aug. 25, 2010 that issued with respect to patent family member Japanese Patent Application No. 2005-506391, along with an English language translation thereof.

* cited by examiner

POROUS COMPOSITE CONTAINING CALCIUM PHOSPHATE AND PROCESS FOR PRODUCING THE SAME

FIELD OF THE INVENTION

The present invention relates to a calcium phosphate-containing porous composite used for artificial bones, scaffolds for cells, dental implant materials, etc., and its production method.

BACKGROUND OF THE INVENTION

Because of excellent compatibility with human bone, artificial bone made of apatite can be directly connected to human bone. Accordingly, artificial bone made of apatite has recently been appreciated for effectiveness, finding clinical applications in cosmetic surgery, neurosurgery, plastic surgery, oral surgery, etc. However, apatite is not necessarily completely identical with human bone in terms of mechanical properties and physiological properties. For instance, an artificial bone made of calcium triphosphate, apatite, etc. is harder and more brittle than human bone. Accordingly, it is difficult to form an artificial bone adapted to an implant site, and the artificial bone is easily detached from the implant site. In addition, while human bone repeatedly undergoes metabolism of absorption and regeneration, artificial bone made of apatite is not substantially dissolved or absorbed in a human body, so that the artificial bone remains in a human body semi-permanently, and that human bone does not grow uniformly in the implanted artificial bone. Accordingly, the remaining artificial bone breaks human bone at an interface with the human bone, making it likely to cause bone fracture.

Research has recently become active on artificial bone decomposable in the human body, which is closer in composition to human bone than the artificial apatite bone, and various proposals have been made. For instance, porous bodies having networks comprising hydroxyapatite, to which collagen and other binders, if necessary, are bonded, were proposed (Japanese Patent 3048289 and JP 11-513590A which is a family member of U.S. Pat. No. 5,776,193). Because these porous bodies are decomposable in a human body, human bone is formed in the porous bodies, and the porous bodies per se are absorbed in a human body. Accordingly, these porous bodies can be used for fixation of vertebra, filling of bone defects, repair of fractured bone, and grafting to jaw bone defects, etc.

The use of a porous body containing a calcium phosphate ceramic, particularly porous apatite having properties close to those of human bone, as a material to be implanted in a living body, provides little likelihood of being rejected by the host, and enjoys a short recuperation period because of high bone-forming capability. Cells participating in the formation of bone are induced in an artificial bone implanted in a bone defect portion, so that human bone grows while the implanted artificial bone is absorbed by the host, resulting in the replacement of the artificial bone by the grown bone tissue.

It has been found, however, that when the implanted artificial bone comes into contact with a soft tissue such as a gum, a subcutaneous tissue, muscle, an internal organ, etc., cells, fibroblasts, etc. in the soft tissue enter into the porous artificial bone, hindering the growth of a bone tissue.

OBJECTS OF THE INVENTION

Accordingly, an object of the present invention is to provide a calcium phosphate-containing porous composite having high bone-forming capability and high affinity to a living body, not hindering the growth of a bone tissue when coming into contact with a soft tissue, and thus suitable for artificial bones, scaffolds for cells, dental implant, etc., and its production method.

DISCLOSURE OF THE INVENTION

As a result of intense research in view of the above object, the inventors have found that the formation of a dense layer on a surface of a porous composite containing a calcium phosphate ceramic substantially prevents tissues and cells not participating in the formation of bone from penetrating into the porous body, thereby accelerating the formation of bone. The present invention has been completed based on this finding.

Thus, the first porous composite of the present invention comprises a porous layer containing a calcium phosphate ceramic, and a dense layer formed on part of the porous layer and having a smaller average pore size than that of the porous layer.

The second porous composite of present invention comprises a porous layer containing a calcium phosphate ceramic, and a dense layer formed on part of the porous layer and having a smaller porosity than that of the porous layer.

The dense layer has an average pore size of preferably 400 µm or less, more preferably 250 µm or less. The porosity of the dense layer is preferably 93% or less, more preferably 90% or less.

The porous composite preferably has a two-layer structure in which the dense layer is formed on the porous layer. The porous composite may have a flange constituted by the dense layer.

The dense layer is preferably constituted by a porous body containing a calcium phosphate ceramic and having a smaller pore size (and/or porosity). The porous body containing a calcium phosphate ceramic, on which the dense layer is formed, is preferably a porous body containing an apatite/collagen composite, with the C-axis of apatite oriented along the collagen fibers. The apatite is preferably hydroxyapatite. The porous body containing a calcium phosphate ceramic may contain a binder. The preferred binder is collagen or gelatin.

In order that the porous composite not only has sufficient mechanical strength, but also retains its shape for a predetermined period of time when implanted in a human body, the porous layer and/or the dense layer are preferably cross-linked.

The first method of the present invention for producing a porous composite comprising a porous layer containing a calcium phosphate ceramic, and a dense layer formed on part of the porous layer at such a position that it comes into contact with a soft tissue when implanted in a human body, the dense layer having a smaller average pore size than that of the porous layer, comprises (1) introducing a slurry containing a calcium phosphate ceramic/collagen composite and collagen into a molding die having a high thermal conductivity, (2) rapidly freezing and drying the slurry in the molding die, to form a porous body comprising a porous layer and a dense layer formed on the porous layer, (3) cross-linking collagen in the porous body, and (4) removing the dense layer except for a portion thereof on a surface coming into contact with a soft tissue when implanted in a human body, so that the porous layer is exposed.

The second method of the present invention for producing a porous composite comprising a porous layer containing a calcium phosphate ceramic, and a dense layer formed on part of the porous layer at such a position that it comes into contact with a soft tissue when implanted in a human body, the dense layer having a smaller average pore size than that of the porous layer, comprises (1) introducing a slurry containing a calcium phosphate ceramic/collagen composite and collagen into a molding die having a cavity comprising a high-thermal conductivity portion and a low-thermal conductivity portion, (2) rapidly freezing and drying the slurry in the molding die, to form a porous body having a dense layer formed on a surface of the porous layer in contact with the high-thermal conductivity portion of the cavity, and (3) cross-linking collagen in the porous body, a surface of the porous body coming into contact with a soft tissue when implanted in a human body being in contact with the high-thermal conductivity portion of the cavity.

DESCRIPTION OF THE PREFERRED EMBODIMENTS

[1] Calcium Phosphate Ceramic-Containing Porous Composite (1) Structure

The porous composite of the present invention comprises a porous layer constituted by a porous body containing a calcium phosphate ceramic, and a dense layer formed on the porous layer and having a smaller average pore size (and/or porosity) than that of the porous layer. The porous composite may have a structure properly selected depending on where it is implanted in a living body.

Figure 1:
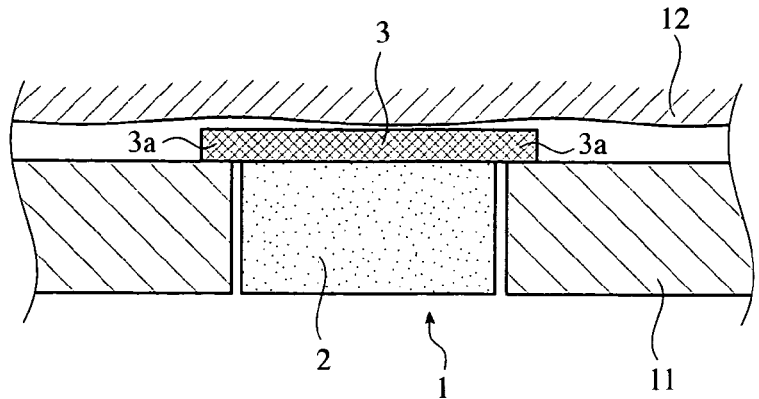
FIG. 1 is a cross-sectional view showing a porous composite according to one embodiment of the present invention, which is introduced into a bone defect portion.

FIG. 1 shows a porous composite according to one embodiment of the present invention, which is introduced into a bone defect portion. The porous composite 1 has a two-layer structure comprising a porous layer 2 and a dense layer 3, the dense layer 3 being positioned on the side of a soft tissue 12 in a bone defect portion. In this example, the dense layer 3 of the porous composite 1 has a flange 3a, so that it can prevent tissues and cells not participating in the formation of bone from entering through a gap between the porous composite 1 and the bone 11.

Figure 2:
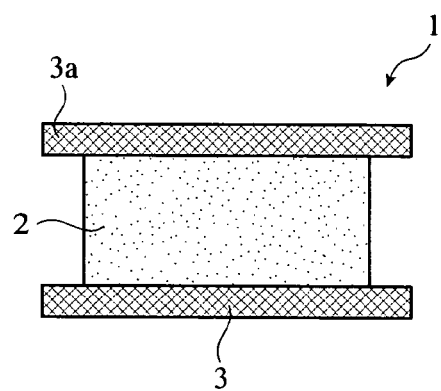
FIG. 2 is a cross-sectional view showing a porous composite according to another embodiment of the present invention.

FIG. 2 shows an example of the porous composite 1 having a structure in which a porous layer 2 is sandwiched by a pair of dense layers 3, 3. Each dense layer 3 may have a flange 3a if necessary, but may not have a flange 3a. The dense layer 3 may be formed on a necessary surface depending on the conditions of the bone defect portion.

Figure 3:
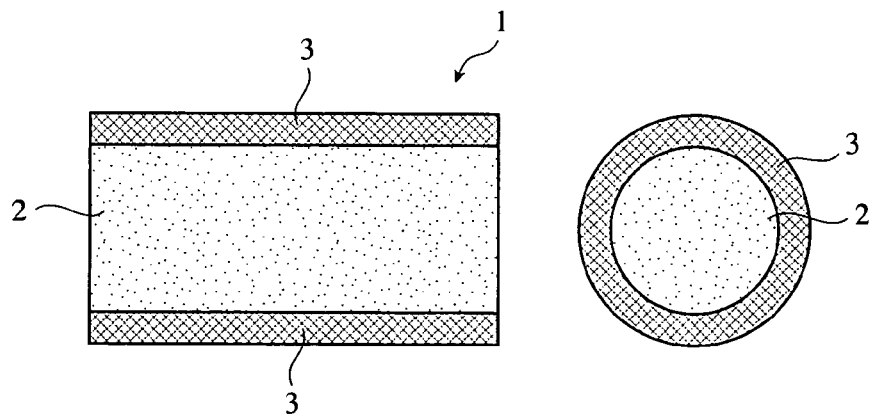
FIG. 3 is a cross-sectional view showing a porous composite according to a further embodiment of the present invention.

FIG. 3 shows an example of the porous composite 1 having a structure in which a cylindrical dense layer 3 covers a porous layer 2. The porous layer 2 is exposed at both ends of the porous composite 1. In this example, the cylindrical dense layer 3 does not have a flange, though it may have a flange if necessary.

Figure 4:
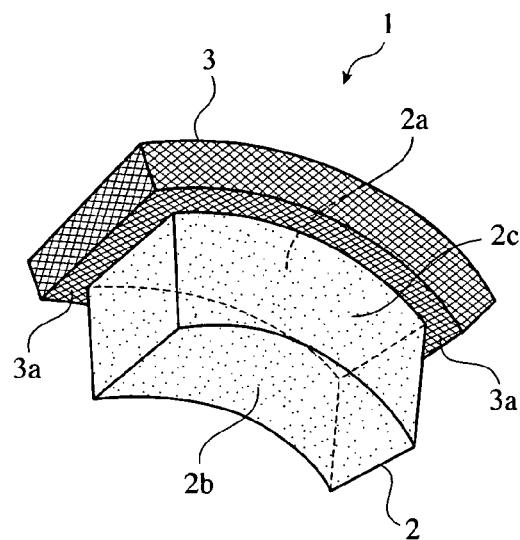
FIG. 4 is a perspective view showing a porous composite (ilium spacer) according to a still further embodiment of the present invention.

The porous composite of the present invention is not restricted to have any one of the shapes shown in FIGS. 1-3, but may have any shape adapted for an implant site. For instance, when used as an ilium spacer, the porous composite of the present invention preferably has a structure comprising a porous layer 2 having a substantially fan-shaped cross section, and a dense layer 3 attached to an outer surface 2a of the porous layer 2 and having an arched cross section, as shown in FIG. 4. The porous layer 2 has a pair of fan-shaped end surfaces (only 2c is visible), and an inner surface 2b in a curved rectangular shape. The dense layer 3 preferably has a flange 3a extending around the porous layer 2.

As shown in the above examples, the porous composite of the present invention has a structure in which the dense layer 3 partially covers the porous layer 2. Accordingly, when it is inserted as an artificial bone into a human body such that the dense layer 3 is positioned on the side of a soft tissue, tissues and cells not participating in the formation of bone are prevented from entering into the porous layer 2, so that the replacement of the artificial bone by a human bone is accelerated.

The dense layer may be as dense as to prevent tissues and cells not participating in the formation of bone from entering into the porous layer. The average pore size of the dense layer is preferably 400 µm or less, more preferably 250 µm or less, further preferably 180 µm or less. The porosity of the dense layer is preferably 93% or less, more preferably 90% or less. The pore size (and/or porosity) need not be uniform in the dense layer, but may have, for instance, such gradation that it gradually increases from the surface to the inside.

The average pore size is determined from pores on a scanning electron photomicrograph (SEM photograph) of the porous layer and the dense layer by an image analysis method. For instance, when the porous layer and the dense layer are composed of hydroxyapatite and collagen, the porosity is determined by the following formula (1):

Porosity (%)=[(Apparent volume−True volume)× 100]/Apparent volume    (1).

The true volume is expressed by mass/density, wherein density $\rho$ is represented by the following formula (2):

$$\rho = (m_A + m_C)/(V_A + V_C) \quad (2)$$
$$= (m_A + m_C)/(m_A/\rho_A + m_C/\rho_C)$$
$$= \rho_A \times \rho_C \times (m_A + m_C)/(m_A \times \rho_C + m_C \times \rho_A),$$

wherein $\rho_A$, $m_A$ and $V_A$ represent the density, mass and volume of hydroxyapatite, and $\rho_C$, $m_C$ and $V_C$ represent the density, mass and volume of collagen.

When the dense layer and the porous layer having the same composition are integrally formed, the dense layer is formed on a higher cooling speed side described below. Accordingly, pores get smaller in the dense layer as nearing its surface, without a clear boundary between the dense layer and the porous layer. Thus, the average pore size of the dense layer is represented herein by an average of measured pore sizes on the dense layer surface. Because how small an average pore size is on the dense layer surface is correlated to how small an average pore size is in the dense layer, a sufficiently small average pore size on the dense layer surface indicates that the inside of the dense layer has a smaller average pore size than that of the porous layer.

The thickness of the dense layer is not particularly restrictive, as long as the dense layer can prevent soft tissues and cells from entering into the porous layer in a human body for a desired period of time, but it is usually about 0.1-5 mm. The pore size and thickness of the dense layer can be controlled to desired levels by adjusting the cooling conditions of the dense layer in the molding of the porous composite.

Because the dense layer prevents tissues and cells not participating in the formation of bone from entering as described above, the average pore size and porosity of the porous layer are not particularly restrictive. However, to accelerate the formation of bone, the average pore size of the porous layer is preferably 1000 μm or less, more preferably 200-800 μm. The porous layer has a porosity of 40-98%, preferably 90-98%.

(2) Composition

The dense layer and the porous layer may be made of the same or different materials. In any case, they are preferably made of bio-decomposable materials.

(a) Dense Layer and Porous Layer Having the Same Composition

Both of the porous layer and the dense layer are preferably made of a calcium phosphate ceramic having high biocompatibility. The porous composite may be made of a calcium phosphate ceramic alone, but preferably contains an organic high-molecular compound from the aspect of softness, elasticity and moldability. The organic compound is preferably decomposed and absorbed in a living body. Preferred examples of such organic high-molecular compounds are bio-decomposable polymers.

The calcium phosphate ceramics may be dibasic calcium phosphate, octacalcium phosphate, tricalcium phosphate, apatites (hydroxyapatite, carbonate apatite, fluoroapatite, etc.), tetracalcium phosphate, etc. Preferable from the aspect of biocompatibility is apatite, particularly hydroxyapatite.

The bio-decomposable polymers may be collagen, gelatin, polylactic acid, polyglycolic acid, copolymers of lactic acid and glycolic acid, polycaprolactone, methylcellulose, ethylcellulose, carboxymethylcellulose, cellulose acetate, dextrose, dextran, chitosan, hyaluronic acid, Ficoll, chondroitin sulfate, polyvinyl alcohol, polyacrylic acid, polyethylene glycol, polypropylene glycol, water-soluble polyacrylate, water-soluble polymethacrylate, etc. Collagen is particularly preferable because it is excellent in softness and moldability, and decomposed and absorbed in a living body.

The collagen may be extracted from animals, etc., though their kinds, parts, ages, etc. are not particularly restrictive. In general, collagen obtained from skins, bones, cartilages, tendons, internal organs, etc. of mammals such as cow, pig, horse, rabbit and rat and birds such as hen, etc. may be used. Collagen-like proteins obtained from skins, bones, cartilages, fins, scales, internal organs, etc. of fish such as cod, flounder, flatfish, salmon, trout, tuna, mackerel, red snapper, sardine, shark, etc. may also be used. The extraction method of collagen is not particularly restrictive but may be a usual one. In place of collagen extracted from animal tissues, collagen produced by gene recombination technologies may also be used. Particularly preferable collagen is atherocollagen obtained by removing immunogenic telopeptide regions from molecular ends by an enzyme treatment.

Both dense layer and porous layer are particularly constituted by an apatite/collagen porous body having different pore sizes (and/or porosities).

(b) Porous Layer and Dense Layer Having Different Compositions

The porous layer is preferably composed of a calcium phosphate ceramic, and the dense layer is preferably composed of a bio-decomposable polymer, which may be the same as described above.

[2] Production Method of Calcium Phosphate Ceramic-Containing Porous Composite (A) Porous Layer and Dense Layer Having the Same Composition Production methods will be explained in detail on the porous composite having a porous layer and a dense layer both constituted by a porous body of a calcium phosphate ceramic/collagen composite.

(1) Structure of Calcium Phosphate Ceramic/Collagen Composite

Though a simple mixture of a calcium phosphate ceramic and collagen may be used, it is preferable to use a calcium phosphate ceramic/collagen composite, in which the calcium phosphate ceramic is chemically combined to collagen, to improve biocompatibility and bone forming. A preferred example of this composite is an apatite/collagen composite having a self-organized structure (similar to the structure of a living bone), in which a C-axis is oriented along collagen fibers. The apatite is most preferably hydroxyapatite. Explanation will be focused below on the apatite/collagen composite, and it is applicable to other composites or porous composites unless otherwise mentioned.

(a) Preparation of Starting Materials for Apatite/Collagen Composite

The apatite/collagen composite can be produced, for instance, by adding an aqueous solution of phosphoric acid or its salt [simply called "phosphoric acid (salt)"] and an aqueous calcium salt solution to a collagen solution. Phosphoric acid or its salts may be phosphoric acid, disodium hydrogenphosphate, sodium dihydrogenphosphate, dipotassium hydrogenphosphate, potassium dihydrogenphosphate, etc. The calcium salts may be calcium carbonate, calcium acetate, calcium hydroxide, etc. The phosphoric acid (salt) and the calcium salt are preferably added in the form of a uniform aqueous solution or suspension.

The fiber length of the resultant apatite/collagen composite can be controlled by a mass ratio of the apatite starting materials [phosphoric acid (salt) and calcium salt] to collagen used. Accordingly, the mass ratio of the apatite starting materials to collagen is properly determined depending on a targeted fiber length of the apatite/collagen composite. A mass ratio of apatite to collagen in the apatite/collagen composite used in the present invention is preferably 9/1 to 6/4, for instance, 8/2.

(b) Preparation of Solution (Dispersion)

First, an aqueous phosphoric acid (salt) solution and an aqueous calcium salt solution or suspension are prepared. Though the concentrations of the aqueous phosphoric acid (salt) solution and the aqueous calcium salt solution or suspension are not particularly restrictive as long as the phosphoric acid (salt) and the calcium salt are at a desired ratio, it is preferable for the convenience of a dropping operation described later that the concentration of the aqueous phosphoric acid (salt) solution is 15 to 240 mM, for instance, about 120 mM, and that the concentration of the aqueous calcium salt solution or suspension is 50 to 800 mM, for instance, about 400 mM.

Collagen is added to the aqueous phosphoric acid (salt) solution generally in the form of an aqueous solution in phosphoric acid. An aqueous solution of collagen in phosphoric acid may contain collagen at a concentration of 0.1 to 1% by mass, for instance, about 0.85% by mass, and phosphoric acid at a concentration of 10 to 80 mM, for instance, about 20 mM.

(c) Production of Apatite/Collagen Composite

Water substantially in the same amount as that of the aqueous calcium salt solution or suspension to be added is charged into a reactor and heated to about 40° C. in advance. An aqueous phosphoric acid (salt) solution containing collagen and an aqueous calcium salt solution or suspension are simultaneously dropped thereinto. The fiber length of the synthesized apatite/collagen composite can be controlled by controlling dropping conditions. The dropping speed is preferably 1 to 60 ml/minute, for instance, about 30 ml/minute. The stirring speed is preferably 1 to 400 rpm, for instance, about 200 rpm.

The reaction solution is preferably kept at pH of 8.9 to 9.1, by keeping the concentration of calcium ions at 3.75 mM or less and the concentration of phosphoric acid ions at 2.25 mM or less in the reaction solution. If the concentrations of the calcium ion and/or the phosphoric acid ion exceeded the above ranges, the self-organization of the composite would be hindered. The above dropping conditions provide the self-organized apatite/collagen composite with a fiber length of 2 mm or less, suitable for a starting material for the cross-linked apatite/collagen porous body.

After completion of dropping, a slurry-like mixture of the apatite/collagen composite and water is dried. The drying may be carried out using a solvent such as ethanol, etc., but it is preferably rapid drying. The rapid drying is carried out while evacuating in a frozen state at −10° C. or lower.

(2) Production of Dispersion Containing Apatite/Collagen Composite

The apatite/collagen composite is mixed with a liquid such as water, an aqueous phosphoric acid solution, etc., and stirred to prepare a paste-like dispersion (slurry). The amount of the liquid added is preferably 80 to 99% by volume, more preferably 90 to 97% by volume, based on 100% by volume of the apatite/collagen composite. The resultant porous body has a porosity P (%), which depends on a volume ratio of the apatite/collagen composite to the liquid in the dispersion as represented by the following formula (3):

$$P=[B/(A+B)]\times 100 \qquad (3),$$

wherein A represents the volume of the apatite/collagen composite in the dispersion, and B represents the volume of a liquid in the dispersion. Accordingly, it is possible to control the porosity P of the porous body by adjusting the amount of the liquid to be added. The fibrous apatite/collagen composite is cut by stirring the dispersion after adding the liquid, resulting in a larger fiber length distribution range, and thus providing the resultant porous body with improved strength.

To obtain a porous composite having a stable three-dimensional shape, a binder is preferably added to the dispersion. The binders may be soluble collagen, gelatin, polylactic acid, polyglycolic acid, copolymers of lactic acid and glycolic acid, polycaprolactone, carboxymethylcellulose, cellulose esters, dextrose, dextran, chitosan, hyaluronic acid, Ficoll, chondroitin sulfate, polyvinyl alcohol, polyacrylic acid, polyethylene glycol, polypropylene glycol, water-soluble polyacrylate, water-soluble polymethacrylate, etc. A particularly preferable binder is collagen. The amount of the binder added is preferably 1-10% by mass, more preferably 3-6% by mass, based on 100% by mass of the apatite/collagen composite.

After adding the binder such as collagen, etc., further stirring is conducted. As in the production of the apatite/collagen composite, the binder is added preferably in the form of an aqueous solution in phosphoric acid. Though the concentration of the binder, etc. are not particularly restricted, it is practically preferable that the concentration of the binder is about 0.85% by mass, and that the concentration of phosphoric acid is about 20 mM.

Because the addition of an aqueous solution of a binder in phosphoric acid (salt) turns the dispersion acidic, a sodium hydroxide solution is added until the dispersion has pH of about 7. The pH of the dispersion is preferably 6.8 to 7.6, more preferably 7.0 to 7.4. By adjusting the pH of the dispersion to 6.8 to 7.6, it is possible to prevent collagen from becoming gelatin in the gelation described later.

The dispersion is mixed with an about 10-times concentrated solution of a physiological buffer saline (PBS) of phosphoric acid to adjust the ionic strength of the dispersion to 0.2 to 1. The more preferred ionic strength is as large as about 0.8, on the same level as that of PBS. Increase in the ionic strength of the dispersion can accelerate collagen added as a binder to form fibers.

Additives such as antibiotics (tetracycline, etc.), chemotherapeutic agents (cisplatin, etc.), bone marrow cells, cell-proliferating factors (BMP, FGF, TGF-β, IGF, PDGF, VEGF, etc.), physiological activation factors (hormone, cytokine, etc.), etc. may be added to the dispersion within a range not hindering the object of the present invention.

(3) Gelation

The dispersion charged into a molding die is kept at a temperature of 35 to 45° C. for gelation. The heating temperature is more preferably 35 to 40° C. For sufficient gelation of the dispersion, the heating time is preferably 0.5 to 3.5 hours, more preferably 1 to 3 hours. With the dispersion kept at 35 to 45° C., the collagen added as a binder forms fibers, thereby turning the dispersion to a gel. The gelled dispersion can prevent the apatite/collagen composite from precipitating therein, thereby producing a uniform porous body. The dispersion subjected to the gelation is in a jelly-like state.

(4) Freeze Drying

After the gelation, the dispersion is frozen for drying. The freeze drying comprises a freezing step and a drying step. In the freezing step, the freezing temperature is preferably −80° C. to −10° C., more preferably −80° C. to −20° C. The size and shape of pores in the porous body can be controlled by a freezing speed. For instance, a larger freezing speed tends to provide smaller pore size to the resultant porous body.

Because the cooling speed differs depending on the thermal conductivity of the molding die, materials are preferably selected for the molding die depending on the desired average pore size. In the case of forming a dense layer having an extremely small average pore size, it is generally preferable to use the molding die made of metals such as aluminum, stainless steel, specialty steel, etc. The molding die may also be formed by materials having different thermal conductivities depending on portions for forming the dense layer.

In the drying step, the dispersion is rapidly dried while evacuating in a frozen state, at −10° C. or lower as in the case of the composite. As long as the dispersion is fully dried, the freeze-drying time is not particularly restricted, though it is preferably about 1-3 days in general. The freeze drying provides a porous body of apatite/collagen.

(5) Cross-Linking

To provide the artificial bone, etc. with increased mechanical strength and shape retention for a desired period of time when implanted in a human body, it is preferable to cross-link the apatite/collagen composite or its mixture with a binder. The cross-linking may be conducted on either one or both of the porous layer and the dense layer.

The cross-linking of collagen may be carried out by any methods such as physical cross-linking methods using γ-rays, ultraviolet rays, electron beams, thermal dehydration, etc., or chemical cross-linking methods using cross-linking agents, condensation agents, etc. In the case of the chemical cross-linking, the freeze-dried porous body is immersed in a cross-linking agent solution to cross-link collagen in the porous body. The chemical cross-linking method is not restricted thereto, but the freeze-dried porous body may be placed in a vapor containing a cross-linking agent, or a cross-linking agent may be added to an aqueous solution or suspension in the production of the apatite/collagen composite.

The cross-linking agents may be, for instance, aldehydes such as glutaraldehyde, formaldehyde, etc.; isocyanates such as hexamethylene diisocyanate, etc.; carbodiimides such as a hydrochloric acid salt of 1-ethyl-3-(3-dimethylaminopropyl) carbodiimide; epoxies such as ethylene glycol diethyl ether, etc.; transglutaminase, etc. Among these cross-linking agents, glutaraldehyde is particularly preferable from the aspects of the easiness of controlling the degree of cross-linking and the compatibility of the resultant cross-linked apatite/collagen porous body with a human body.

When glutaraldehyde is used as the cross-linking agent, the concentration of a glutaraldehyde solution is preferably 0.005 to 0.015% by mass, more preferably 0.005 to 0.01% by mass. The cross-linked apatite/collagen porous body should be dehydrated. When alcohol such as ethanol, etc. is used as a solvent for a glutaraldehyde solution, the dehydration can be conducted simultaneously with the cross-linking of collagen. A cross-linking reaction occurs in a state where the apatite/collagen composite is contracted, by conducting the dehydration and the cross-linking simultaneously, so that the resultant cross-linked apatite/collagen porous body can have improved elasticity.

After the cross-linking, the cross-linked apatite/collagen porous body is immersed in aqueous solution of about 2% by mass of glycine to remove unreacted glutaraldehyde, and then washed with water. The cross-linked apatite/collagen porous body is further immersed in ethanol for dehydration, and then dried at room temperature.

(6) Working

The cross-linked apatite/collagen porous body thus obtained has a structure in which a dense layer is integrally formed on the porous layer surface. A desired portion of the dense layer on the surface of the resultant porous composite can be machined by a lathe, etc., to form a portion having the dense layer and a portion on which the porous layer is exposed. The porous composite is finally sterilized by ultra-violet rays, γ-rays, electron beams, heat drying, etc.

(7) Principle of Forming Dense Layer

Why the porous composite integrally having a dense layer having a smaller pore size (and/or porosity) on a surface portion by freeze-drying a dispersion containing the apatite/collagen composite in a molding die is that a slurry portion closer to the cavity surface of the molding die is cooled more rapidly than inside the slurry, resulting in finer ice crystals, and thus finer pores left after the evaporation of ice. Accordingly, the pore size can be controlled by adjusting the cooling speed during freezing.

Also, by cooling a desired portion of the cavity surface of the molding die more rapidly than the other portion, it is possible to partially form a dense layer having a smaller pore size (and/or porosity). For instance, with a first portion of the slurry in contact with a metal (aluminum, stainless steel, specialty steel, etc.) having high thermal conductivity, and a second portion of the slurry in contact with a plastic having lower thermal conductivity, a cooling speed can be higher in the first portion than in the second portion, thereby forming a dense layer only in the first portion.

(B) Porous Layer and Dense Layer Having Different Compositions

The formation method of the dense layer may be properly selected depending on materials used, etc. For instance, the porous layer and the dense layer are separately produced and then bonded by an adhesive, etc. Alternatively, a dense layer may be formed on part of the porous layer produced in advance.

When the calcium phosphate ceramic-containing porous composite comprises a porous block of calcium phosphate ceramic, it may be produced by the method described in JP 2-167868A or JP 8-48583A. The production method of a porous ceramic described in JP 2-167868A comprises foaming a slurry or flowable gel comprising calcium phosphate powder and a high-molecular weight material by stirring, casting the foamed slurry or flowable gel, heating the slurry or flowable gel to increase its viscosity or to cause gelation, thereby fixing pores, and baking the resultant foamed product if necessary. The production method of the porous ceramic described in JP 8-48583A comprises compression-molding a mixture of calcium phosphate powder and polysaccharide particles, and baking the resultant compressed powder.

The present invention will be explained in more detail with reference to Examples below without intention of restricting the scope of the present invention.

EXAMPLE 1

460 g of a solution containing 0.8% by mass of collagen and 100 mM of phosphoric acid was added to 340 ml of pure water, to prepare a solution A. 23 g of calcium hydroxide was added to 380 ml of pure water and stirred to prepare a solution B. The solution A and the solution B were simultaneously dropped into a vessel containing 400 ml of pure water while adjusting pH to 9 by a pH controller, to prepare a solution containing composite fibers of hydroxyapatite and collagen. This solution was frozen in a freeze-drying apparatus, and then dried over 7 days, to obtain a fibrous hydroxyapatite/collagen composite having an average length of about 1-2 mm.

3.6 g of pure water was added to 1 g of the dried fibrous hydroxyapatite/collagen composite and stirred, to obtain a paste-like dispersion. After 4 g of aqueous solution containing 0.8% by mass of collagen and 20 mM of phosphoric acid was added to the paste-like dispersion and stirred, 1-N NaOH was added thereto until its pH became substantially 7. 10-times concentrated PBS was then added to the dispersion until its ionic strength became 0.8.

Figure 5A:
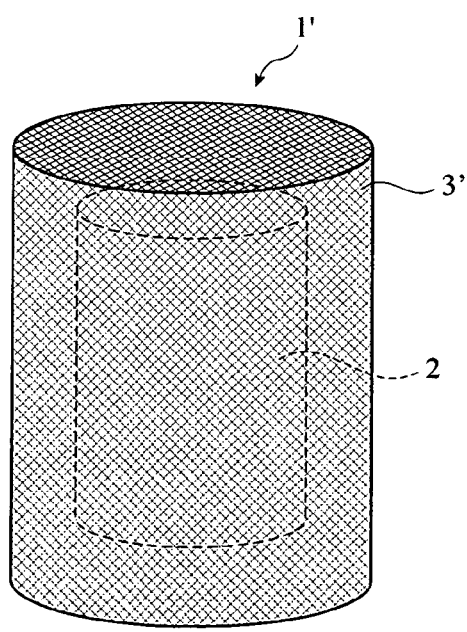
FIG. 5(a) is a perspective view showing a cross-linked hydroxyapatite/collagen porous body obtained in Example 1.

The resultant dispersion was introduced into a molding die made of stainless steel, and kept at 37° C. for 2 hours for gelation, resulting in a jelly-like molded product. This molded product was frozen at −20° C., and dried over 3 days. A solution of 0.01% by mass of glutaraldehyde in ethanol having a purity of 99.5% as a solvent was prepared, and the molded product was immersed in this solution to cross-link the collagen. The resultant cross-linked, porous body was washed with water, immersed in a 2-%-by-mass glycine solution to remove the unreacted glutaraldehyde, and washed with water again. Thus, a cross-linked hydroxyapatite/collagen porous body 1' having a dense layer 3' on the entire surface as shown in FIG. 5(a) was obtained.

Figure 5B:
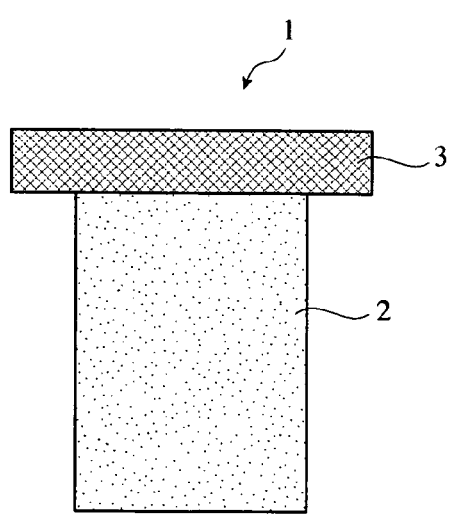
FIG. 5(b) is a cross-sectional view showing a porous composite obtained by removing dense layers in side and bottom surfaces from the cross-linked hydroxyapatite/collagen porous body of FIG. 5(a).

Among the dense layer 3' of the cross-linked hydroxyapatite/collagen porous body 1', those on a side surface and a bottom surface were removed by machining, leaving a dense layer 3' on an upper surface intact, thereby obtaining a porous composite 1 having a flanged dense layer portion 3 on an upper surface with the porous layer 2 exposed on both side and bottom surfaces as shown in FIG. 5(b). The dense layer portion 3 was as thick as about 2 mm. The average pore sizes of the porous layer 2 and the dense layer portion 3 were determined from the SEM photograph. The porosities of the porous layer 2 and the dense layer portion 3 were determined by the following formula (2):

Porosity (%)=[(Apparent volume−True volume)× 100]/Apparent volume       (2).

The definition of the formula (2) is as described in [1] (1).

It was thus found that the average pore size was 60 µm in the dense layer portion 3 and 600 µm in the porous layer 2, and that the porosity was 90% in the dense layer 3 and 95% in the porous layer 2.

EFFECT OF THE INVENTION

Because the porous composite of the present invention has a dense layer having a smaller pore size (and/or porosity) than that of a porous layer on part of its porous layer surface, tissues and cells not participating in the formation of bone are prevented from penetrating into the porous layer when implanted in a human body, so that it can exhibit excellent bone-forming capability. Accordingly, the porous composite of the present invention is suitable for biomaterials such as artificial bones (ilium spacers, bone fillers to tumor-removed portions, etc.), artificial joints, materials for connecting tendons to bones, dental implant materials, scaffolds for living tissues and cells, etc.

What is claimed is:

1. A porous composite comprising a porous layer, and a dense layer formed on part of said porous layer and having a smaller average pore size or porosity than that of said porous layer, wherein said dense layer comprises a flange extending from a surface of the porous layer, and said flange and said porous layer are integral and of one-piece construction, and wherein said porous layer and said dense layer consist essentially of a hydroxyapatite/collagen composite and a collagen binder, and said porous layer has a porosity of 90-98%.

2. The porous composite according to claim 1, wherein said dense layer has a porosity of 93% or less.

3. The porous composite according to claim 1, wherein said dense layer has an average pore size of 400µm or less.

4. The porous composite according to claim 1, having a two-layer structure in which said dense layer is formed on said porous layer.

5. The porous composite according to claim 1, wherein said hydroxyapatite has a C-axis oriented along collagen fibers.

6. The porous composite according to claim wherein said porous layer and/or said dense layer are cross-linked.

7. The porous composite according to claim 1, wherein said porous layer is sandwiched by a pair of dense layers.

8. A method for producing the porous composite of claim 2 comprising (1) introducing a slurry containing a hydroxyapatite/collagen composite and collagen into a molding die having a high thermal conductivity, (2) rapidly freezing and drying said slurry in said molding die, to form a porous body comprising a porous layer and a dense layer formed on said porous layer, (3) cross-linking collagen in said porous body, and (4) removing said dense layer except for a portion comprising said dense layer comprising said flange, on a surface structured and designed to come into contact with a soft tissue when implanted in a human body, so that said porous layer is exposed.

9. A method for producing the porous composite of claim 2 comprising (1) introducing a slurry containing a hydroxyapatite/collagen composite and collagen into a molding die having a cavity comprising a high-thermal conductivity portion and a low-thermal conductivity portion, (2) rapidly freezing and drying said slurry in said molding die, to form a porous body comprising a porous layer and a dense layer formed on a surface of said porous layer in contact with the high-thermal conductivity portion of said cavity, and (3) cross-linking collagen in said porous body, said dense portion comprising said flange structured and designed to come into contact with a soft tissue when implanted in a human body being in contact with the high-thermal conductivity portion of said cavity.

10. The porous composite according to claim 2, wherein said hydroxyapatite has a C-axis oriented along collagen fibers.

11. A porous composite comprising a porous layer, and a dense layer formed on part of said porous layer and having a smaller average pore size or porosity than that of said porous layer, wherein said dense layer comprises a flange extending from a surface of the porous layer, and said flange and said porous layer are integral and of one-piece construction, and wherein said porous layer and said dense layer consist essentially of a hydroxyapatite/collagen composite and a collagen binder, and at least one of said dense layer and said porous layer further comprising at least one of the following additives: an antibiotic, a chemotherapeutic agent, bone marrow cells, cell-proliferating factors, and a physiological activation factor, and said porous layer has a porosity of 90-98%.

* * * * *